(12) United States Patent
Zhu et al.

(10) Patent No.: US 7,249,520 B1
(45) Date of Patent: Jul. 31, 2007

(54) SELF-LOADED PENDULUM FOR SLIDER FLEXURE STIFFNESS MEASUREMENTS

(75) Inventors: Li-Yan Zhu, San Jose, CA (US);
Gautham Gowda, Milpitas, CA (US);
Chao-Hui Yang, Milpitas, CA (US)

(73) Assignee: SAE Magnetics (HK) Ltd., Shatin, N.T. (HK)

( * ) Notice: Subject to any disclaimer, the term of this patent is extended or adjusted under 35 U.S.C. 154(b) by 0 days.

(21) Appl. No.: 11/522,182

(22) Filed: Sep. 15, 2006

(51) Int. Cl.
*G01B 7/30* (2006.01)

(52) U.S. Cl. .......................... 73/760; 73/779; 360/244; 324/207.15

(58) Field of Classification Search ................. 73/760, 73/779, 865.9; 360/244; 324/207.11–207.19; G01B 7/14
See application file for complete search history.

(56) References Cited

U.S. PATENT DOCUMENTS

| | | | | |
|---|---|---|---|---|
| 5,811,700 A | * | 9/1998 | Schudel | 73/865.9 |
| 6,914,752 B2 | * | 7/2005 | Albrecht et al. | 360/246.1 |
| 7,069,156 B2 | * | 6/2006 | Zeng | 702/43 |
| 7,136,260 B2 | * | 11/2006 | Oh et al. | 360/244.8 |
| 7,146,863 B2 | * | 12/2006 | Furui | 73/847 |
| 2003/0007292 A1 | | 1/2003 | Himes et al. | |
| 2003/0009898 A1 | | 1/2003 | Slocum et al. | |
| 2005/0190500 A1 | * | 9/2005 | Song | 360/235.5 |
| 2005/0280940 A1 | * | 12/2005 | Kamigama | 360/234.6 |
| 2006/0050441 A1 | * | 3/2006 | Kang | 360/245.1 |

OTHER PUBLICATIONS

"Slider Pitch Moment Associated with Dimple Friction", by Li-Yan Zhu et al., to be published in ASME J. Tribology, TRIB2004-64251 (Final), SAE Magnetics (H.K.), US Office 100 S. Milpitas Blvd., CA 95035, USA.

* cited by examiner

*Primary Examiner*—Edward Lefkowitz
*Assistant Examiner*—Jonathan Dunlap
(74) *Attorney, Agent, or Firm*—Saile Ackerman LLC; Stephen B. Ackerman

(57) ABSTRACT

A device is provided by which the stiffness coefficient of a flexure, in either a pitch or roll direction, can be measured while a slider is mounted thereon and while the flexure and slider are in a loaded condition as might be obtained during normal operational conditions of a HGA in a HDA. There are two methods of making the measurement, a static method in which the slider is loaded by an external weight called a pendulum and the angular displacement of the slider is measured, and a dynamical method in which the pendulum is caused to oscillate while in contact with the slider and its natural and loaded frequencies of oscillation are measured.

25 Claims, 3 Drawing Sheets

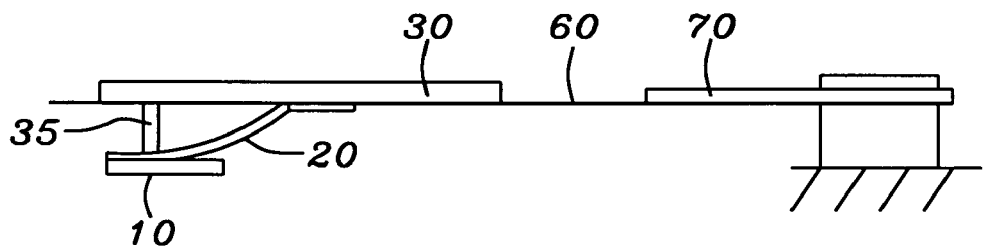
FIG. 1 – Prior Art
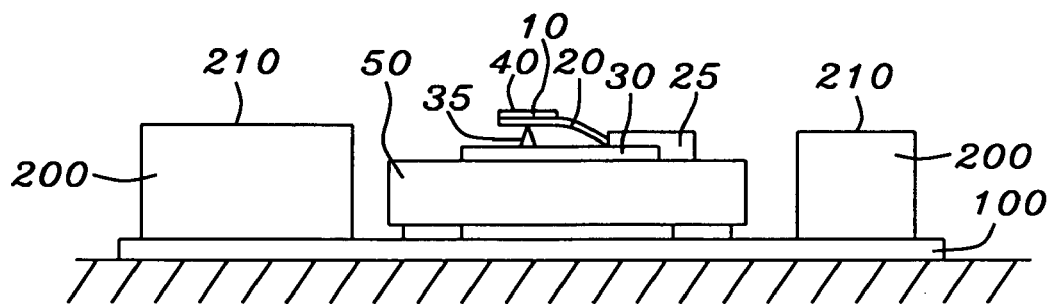
FIG. 2a
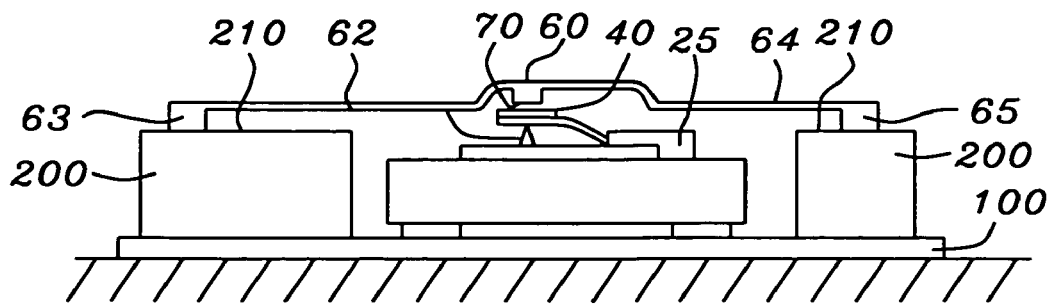
FIG. 2b

SELF-LOADED PENDULUM FOR SLIDER FLEXURE STIFFNESS MEASUREMENTS

BACKGROUND OF THE INVENTION

1. Field of the Invention

This invention relates to the design of a hard disk drive (HDD) suspension that includes a slider mounted on a flexure. More particularly, it relates to a device and method using the device for measuring the flexure stiffness under load conditions.

2. Description of the Related Art

A hard disk drive (HDD) uses an encapsulated thin film magnetic read/write head (transducer), called a slider, to read and write data on a magnetic medium or storage disk. The slider has a pre-patterned air-bearing surface (ABS) and is a part of a flexible head gimbals assembly (HGA). Looking at FIG. 1, there is shown a highly schematic side view of a prior art HGA. The slider (10) is mounted on a gimbal assembly or flexure (20), The flexure is affixed to a relatively rigid loadbeam (30). The loadbeam exerts a downward force on the flexure through a downward pointing protrusion called a dimple (35). The loadbeam is connected to a base-plate (70) through a pivot or bend-zone (60). The combination of the loadbeam, the gimbal assembly (referred to herein as a flexure), the electrically conducting leads (or traces) (not shown), the pivot and a base-plate, is collectively termed the suspension. The suspension is activated by a servo actuator and associated electronic control circuitry to position the slider at various locations along the magnetically encoded tracks on the disk. As the disk is rapidly rotated by a spindle motor, hydrodynamic pressure causes an air flow between the ABS of the slider and the surface of the disk. This flow lifts and suspends the slider so that it literally flies above the surface of the disk (at a "fly height" of approximately 10 nm) on a layer of air called, appropriately, the air-bearing layer. The edge of the slider into which the disk rotates is called its "leading edge," the opposite edge, which contains the read/write head is called the "trailing edge." The loadbeam, as is known in the art, has a small downward extending protrusion or "dimple" ((35) in FIG. 1) formed on its disk-facing side that presses against the backside of the slider at a contact point, providing a downward force (typically 2.5 grams) and serving as a pivot for the slider to rotate about. This suspension system of loadbeam and gimbal provides mechanical support for the slider while also allowing the slider pitch and roll capability when fly height is achieved. In addition, the system provides an electrical connection (i.e., a placement for the routing of conducting traces) between the read/write head and the pre-amplifier.

In an operating disk drive the slider is "loaded" by its position over a rapidly spinning disk (i.e., the slider is placed under a combination of forces as a result of upward hydrodynamic pressure from the air bearing layer and mechanical downward forces). The downward component of the load force is due to elastic deformation of the suspension at the bend zone (shown in FIG. 1). This force is transmitted to the slider through the dimple that contacts the flexure.

The ABS of the slider is virtually parallel to the surface of an operationally spinning disk (well within 1 mrad of horizontal). However, when the slider is unloaded the ABS orientation is no longer a result of disk rotation and it deviates from its flying attitude. This deviation, referenced to the loadbeam orientation, is known as static attitude. It consists of two components, pitch static attitude (PSA) and roll static attitude (RSA). Corresponding to PSA, the flexure exhibits a pitch stiffness ($k_p$). The product of PSA and $k_p$ represents a pitch moment exerted by the flexure on the flying slider.

Enabling the slider to fly in a stable manner above the disk places stringent requirements on the suspension design, such as providing a proper range of its vertical stiffness (Kz), gimbal (flexure) pitch and roll stiffness (Kp, Kr), gimbal pitch/roll static attitude (PSA/RSA), operational shock performance (G/gram) and the like. These requirements are mainly static and based on system geometry.

The flexure pitch stiffness increases when a load-force is applied through the loadbeam dimple to the slider. Traditional stiffness measurements are made in the absence of load forces. Such measurements are inaccurate for the purposes of slider air bearing surface (ABS) design, because the stiffness may increase significantly when the slider is loaded. Applying a load-force through mechanical contact is difficult, as any misalignment of the contact will affect the measurement. Unfortunately, there is no easy method to detect and correct such misalignment error. Similarly, friction at the ABS, caused when the load-force impedes slider motion in the plane of the ABS, also affects the measurement. This important friction term is statically indeterminate. Note that the physics of a flexure mounted slider under load, including the effects of dimple friction, is presented in "Slider Pitch Moment Associated with Dimple Friction" by Li-Yan Zhu, Chao-Hui Yang, Yen Fu and Ellis Cha, to be published in ASME J. Tribology, which is fully incorporated herein by reference.

A prior-art approach to measuring pitch and/or roll stiffness is to shake the HGA and measure the resulting slider resonance frequencies. Although a load-force similar to the "gram-load" present under actual operating conditions cannot be exerted, a small spring force, known as the dimple contact force (DCF), prevents dimple slip when the vibration amplitude is very small. Thus the "loaded" pitch stiffness can be calculated. This method, however, can only measure the pitch stiffness when the slider pitch is equal to its PSA. It cannot measure pitch stiffness at the flying condition, which is nearly zero pitch. Furthermore, this method does not fully reflect the contribution of dimple curvature to pitch and roll moments.

Another prior-art approach is to support the slider by two or more separate load cells. The nominal load force can be exerted by the load beam. The slider pitch and roll angles can be adjusted by translating at least one load cell. The pitch and roll moments can be calculated by multiplying the distance between two load cells by the difference in load forces exerted on the load cells. However, as described above, friction on the slider ABS is very difficult to assess and compensate.

The prior art does not disclose a significant number of methods for measuring flexure stiffness under the full gram load. The importance of stiffness, however, is well recognized in the prior art. Himes et al. (US Published Patent Application 2003/0007292) discusses the need for reducing stiffness at various points in the structure of the HGA. In particular, Himes teaches the fabrication of a low stiffness printed circuit interconnect to enable electrical connectivity within the HGA assembly. A method of measuring the stiffness of small assemblies, not specifically directed to flexures, is taught by Slocum et al. (US Published Patent Application 2003/0009898). Slocum teaches a method of applying a probe to an end of a flexible member and pushing the member while the displacement of the member is measured. Because of misalignment difficulties mentioned above, this method does not seem appropriate for measuring the stiffness of a flexure under actual loading conditions encountered during disk drive operation.

It is clear that a novel method is needed to overcome the shortcomings of the prior-art methodology and such a method will be presented herein.

SUMMARY OF THE INVENTION

A first object of the present invention is to provide a method for measuring flexure pitch stiffness under operating conditions when a load-force is applied to the slider and the slider is at its flying condition of nearly zero pitch.

A second object of this invention is to provide such a method that can measure average and local flexure stiffness with any gram-load and at any pitch and roll angle.

A third object of the present invention is to provide a method that is free of ABS friction and is, therefore, more accurate and easier to operate.

A fourth object of the present invention is to provide such a method that does not require expensive apparatus such as a laser doppler interferometer that is needed for traditional vibrational methods.

A fifth object of the present invention is to provide such a method that eliminates load-force misalignment.

This object will be met by placing a pendulum, whose weight equals the desired load-force, directly above and in intimate contact with the slider ABS, while the HGA load-beam is firmly supported underneath. In one preferred embodiment, the center of mass of the pendulum is carefully positioned just below the point of contact between the loadbeam dimple and the flexure. In this implementation of the invention, the slider (and flexure) is caused to deflect by tilting the load-beam. The ratio of load-beam deflection to slider deflection is used to calculate the average pitch stiffness in the range of pendulum deflection.

In a second preferred embodiment, the pendulum is made to contact the slider ABS and is adjusted to achieve a desired pitch angle. The pendulum is then allowed to oscillate freely while in contact with the slider and, thereby, while experiencing the stiffness of the flexure. Its oscillation frequency is measured by a non-contact displacement sensor and that result is used to calculate the local stiffness at that desired pitch angle.

BRIEF DESCRIPTION OF THE DRAWINGS

The objects, features, and advantages of the present invention are understood within the context of the Description of the Preferred Embodiment as set forth below. The Description of the Preferred Embodiment is understood within the context of the accompanying figures, wherein:

FIG. 1 (prior art) is a schematic side view of a simple model of a flexure mounted slider mounted on a load beam and maintained in a flexed position by the load beam dimple.

FIG. 2a-FIG. 2d is a series of schematic diagrams showing portions of the measuring apparatus used to achieve the objects of the invention and its use.

DESCRIPTION OF THE PREFERRED EMBODIMENTS

Figure 2C:
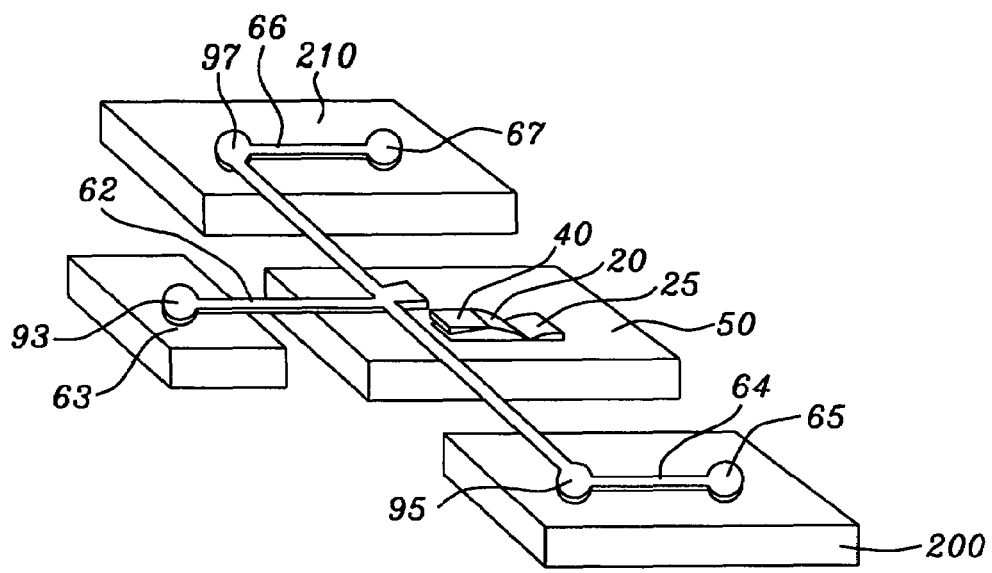

The preferred embodiments of this invention provide a device and two methods using the device for measuring the pitch and/or roll stiffness of a flexure mounted slider under what are essentially the operating conditions wherein a load force is applied to the slider and the slider ABS is at nearly zero pitch. The friction at the ABS is negligible during the measurement.

Flexure stiffness in the pitch direction is sensitive to the dimple contact condition. Because the load force hinders dimple slip, the flexure pitch stiffness is increased. Furthermore, the flexure pitch stiffness at loaded (no dimple-slip) condition depends on the pitch angle, which affects the flexure height profile. In addition, the true radius of curvature of the dimple contributes to the flexure stiffness in direct proportion to the load force. Assuming an ideal pin-point dimple contact, gram load has very little effect on flexure roll stiffness, because the flexure has very little tendency to slip in the roll mode. In other words, the flexure roll stiffness is insensitive to gram load and static attitudes (slider pitch and roll angle). The flexure pitch stiffness varies with static attitudes and is generally higher in the presence of gram load. For the slider ABS design, we are always interested in the flexure stiffness under the gram load. In particular, we are interested in the following two aspects of pitch stiffness:

1. The pitch moment associated with pitch static attitude (PSA), which affects the fly height (FH) target and is equivalent to the average pitch stiffness between flying pitch (nearly zero) and static pitch (typically between 1° and 2° away from the flying pitch).

2. Local pitch stiffness at PSA, which affects FH sensitivity to PSA distribution.

Measuring Device and Measuring Procedure:

To accomplish the objects of the invention, a measuring device and a measuring procedure using that device are described in the following sequence of figures. Referring first to highly schematic FIG. 2a, the load beam (30) is shown lightly clamped on a fixture (25), with its dimple (35) contacting the flexure (20) from below and the ABS (40) of the slider (10) facing up. The fixture is mounted firmly on a movable lifting mechanism that will be called a lift (50) for the purposes of this description. The lift includes three translational micrometer stages (not shown) capable of moving the lift (and the fixture affixed thereto) in three orthogonal directions. In particular, the fixture can be positioned in a horizontal plane and raised vertically. The lift is mounted on a baseplate (100) that can be tilted slightly from the horizontal by means of a shim ((110) in FIG. 2d) or other adjustment. The lift is substantially surrounded by a dock (200) having planar surfaces (210), which is also mounted on the baseplate (100) and, as will be seen later, will serve as a foundation for supporting other parts of the measuring device. The movement of the lift will be relative to the dock. In this embodiment, the planar surfaces of the dock (210) are polished and mirror-like to enhance the visibility of certain measurement processes, but they need only be smooth and planar.

Referring to FIG. 2b, there is shown schematically the device of FIG. 2a with the addition of a moveable rigid body that will be denoted a pendulum (60). A load force on the slider ABS (40) can now be provided by contacting the slider ABS with a flat surface of the pendulum, denoted a facet (70) and allowing the weight of the pendulum to be supported by the ABS. The ability to measure the stiffness of the flexure while the slider is under this load is a part of the invention. During the measuring process the weight of the pendulum will be supported by the slider/flexure and, in that way, the desired load to the slider is provided.

Before the actual measuring process occurs, as illustrated in the configuration of this figure, the pendulum is supported on the dock by three limbs, only two being shown in this perspective (62), (64). Each limb terminates in a foot (63), (65). The feet rest on the planar surfaces of the dock (210).

Referring to FIG. 2c, there is shown an overhead perspective view of the pendulum in which the limb configuration, including the third limb (66) is more easily seen.

In the present configuration, two of the limbs are bent (64), (66) to avoid interference with the flexure (20) and the lift (50). Each foot (63), (65), (67) has a small tip or protrusion on its underside (not shown) so it can rest on a smooth surface (the surface of the dock (210)) without an undue adhesion or suction force (called stiction). It should be noted that the overall shape of the pendulum may be different corresponding to various possible configurations of the tester. The mirror-like surface of the dock will allow the positions of the feet of the pendulum to be seen as they move on the dock surface.

Also shown in FIG. 2c are small regions, called targets (93), (95), (97), located on the pendulum. The displacements of these targets, will be measured as the process proceeds. As will be seen in FIG. 2d, measuring the displacement of the targets will be achieved by the use of an induction sensor placed adjacent to the target whose displacement is being measured. Any target located on the roll-axis of the pendulum (an axis about which the slider rolls and which, therefore, does not itself roll) is insensitive to the roll motion and it is called a roll target. Any target located on the pitch axis (an axis about which the slider engages in pitch motion and which, therefore, does not itself engage in pitch motion) is insensitive to pitch motion and is called a pitch target. Any target located off both the pitch and roll axes are sensitive to both pitch and roll motions and are called mixed targets. An inductive transducer (e.g. Omega LD701-1/2) Linear Displacement Sensor) was chosen for displacement measurements, but other displacement measuring devices are suitable.

As noted above, the pendulum has a down-facing flat surface called a facet (70). In the static measurement to be described below, the facet is directly above the center of mass (CM) of the pendulum and it engages the slider ABS (40) to load the slider. The facet should be sufficiently rough to avoid stiction with the ABS. It should also be free of plateaus and trenches whose dimensions are comparable with the ABS rail, pad or cavity dimensions (surface structures on the ABS). The pendulum may be an integral metal (non-ferromagnetic) piece or an assembly of multiple parts. It can have a fixed CM or an adjustable CM and the CM can be above or below the facet, depending upon the particular measurement being carried out. The non-ferromagnetic nature of the pendulum assures that it is not affected by ambient magnetic fields.

As noted above, the pendulum is presented to the lift by means of a dock (200). The dock supports the pendulum while the lift, together with the slider and flexure affixed to it, moves upward relative to the pendulum to enable the pendulum facet to contact the ABS and cause the slider to be loaded. The surface of the dock on which the feet of the pendulum will rest is preferably smooth and reflective (mirror-like) to enhance the ability to detect vertical motion of the pendulum feet by the naked eye as the testing procedure is carried out. A mirror-like surface is not necessary however. The dock may be stationary, or it may have an optional mobility in the vertical direction to make inspection and service convenient. The lift (50) and the dock (200) are both mounted firmly on a common base-plate (100), but as noted above the lift moves relative to the dock.

Figure 2D:
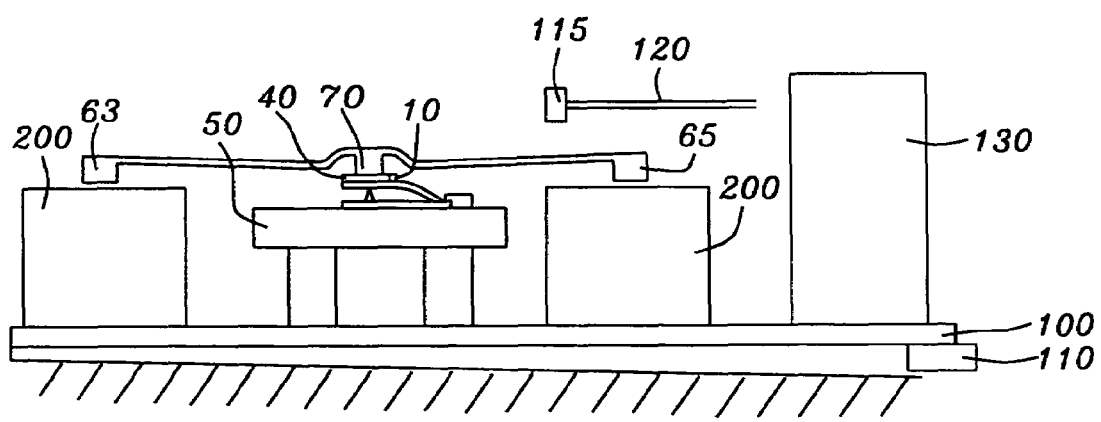

Referring to FIG. 2d there is shown, schematically, the device of FIG. 2c and FIG. 2b with the addition of a displacement sensor (115) that, in this embodiment, is mounted on a rigid cantilever (120) that extends outward from a massive rectangular block (130). The block can be placed on the base plate (100) without any fastener so that it is free to be moved by hand to access any of the targets on the pendulum. It is noted that other sensor configurations are equally suitable. In this figure, the pendulum is shown in a position corresponding to the performance of a measurement, in which all the feet ((65) and (63) being shown) are lifted from the dock and the full weight of the pendulum is loading the slider (10).

The base plate (100) normally rests on a horizontal surface and no isolation from floor vibration is needed in ordinary laboratories. A transparent enclosure (not shown) is needed to shield the tester from air turbulence. For static measurements, to be described below, the inclination of the base plate needs to be adjusted within a range between +/−5°. This can be achieved by the insertion of a shim (110) beneath a base plate edge or by the addition of an adjustment screw (not shown).

To describe, schematically, how the measuring process actually proceeds we return to FIG. 2a. In this figure, the pendulum has not yet been placed on the dock (200), but the flexure mounted slider (10) is already affixed to the lift. At this point, the vertical micrometer stage in the lift is turned to raise the lift so that the slider ABS (40) is below the expected facet height when the pendulum is placed on the dock, as in FIG. 2b. We will denote as position 1 the position of the ABS (40) as shown in FIG. 2a.

Referring to FIG. 2b (and, for another view, to FIG. 2c), we see the pendulum now placed on the dock (200), supported by its three feet (63), (65), (with (67) not shown) which are placed on the mirror-like surfaces (210) of the dock.

Referring to FIG. 2d, we see the configuration of FIG. 2b with the lift having been slowly raised (vertically) so that the slider ABS (40) forcefully engages the pendulum facet (70) and that at least one of the pendulum feet lifts up from the dock. Note, in the figure, both visible feet (63) and (65) are shown lifted from the dock (200). The mirror-like surface of the dock in this embodiment makes the lifting of the foot easy to see. At this point in the measuring process a displacement sensor (115) has also been placed on the baseplate and is free to move. The sensor, in this embodiment, is mounted by a cantilever (120) to a block (130) that is placed on the base-plate adjacent to one of the targets on the pendulum whose displacement is to be measured.

After the lifting of at least one foot, the lift is then lowered so that it is returned to position 1. The horizontal micrometer stages are then manipulated so that the slider ABS moves laterally away from the foot that rose. Repeating the sequence, the lift is raised again, to see which leg now raises first. The process is repeated until the horizontal placement of the lift is such that the three feet of the pendulum lift simultaneously when the facet engages the ABS. This is the configuration shown in FIG. 2d, wherein all feet of the pendulum have lifted from the dock and the slider is properly loaded. In this position, the load force is correctly aligned with the dimple.

Static Measurement

Figure 3:
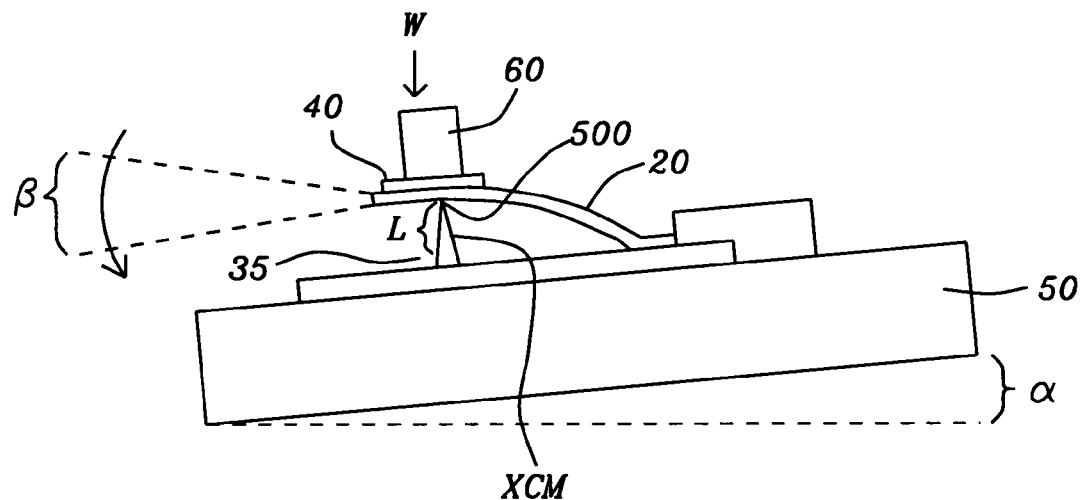
FIG. 3 is a schematic illustration of the relevant angles that are measured to determine the stiffness.

Referring to FIG. 3, we see a schematic illustration of the pendulum in correctly aligned loading contact with the slider ABS (40) subsequent to having all of its feet lifted simultaneously as in FIG. 2*d*. Let the entire pendulum now be represented schematically by the rectangle (60) and let the weight of the pendulum be denoted W with a downward arrow (typically providing a 2.5 gram force) and let the pendulum CM, denoted by an X, be a distance L below the dimple contact (500) with the underside of the flexure (20). When the base plate (and the lift with it) is now tilted in the pitch direction through a measurable angle α as shown in the figure (measured using a spacing sensor fixed to the baseplate and not shown in the figure), the ABS and the pendulum along with it is caused to tilt through an angle β (measured using the displacement sensor at the target, which is not shown). The flexure is now in a condition of static equilibrium. The difference:

$$\theta = \alpha - \beta$$

is, therefore, empirically determinate.

The condition of static equilibrium of the flexure can be expressed as:

$$k_p \theta = WL \sin(\alpha - \beta), \quad (1)$$

at the desired angle of pitch change, where $k_p$ is the pitch stiffness. Rearranging terms in (1) and taking the inverse sine:

$$\alpha = \theta + \sin^{-1}(k_p \theta / WL) \quad (2)$$

For small θ, the above equations are linearized and yield a flexure pitch stiffness, $k_p$, that is given approximately by:

$$k_p \approx WL\beta/\theta = WL(\alpha/\theta - 1). \quad (3)$$

As can be seen in (3), all the measurable angles have been obtained from which the desired value of $k_p$ can be calculated. The measurement of roll stiffness, $k_r$, is similarly performed and is, therefore, not indicated herein Dynamic Measurements Referring back to FIG. 2*d*, the loadbeam is again firmly attached to a stationary support as in FIG. 2*d*, and a pendulum is contacting the ABS of the slider with the pendulum adjusted so that all its feet lift from the dock simultaneously. Unlike the static measurement process described in FIG. 3, the baseplate is not tilted but the pendulum is now made to oscillate in either a pitch or a roll direction. It is noted that the pendulum used in the dynamic measurement may not be the same pendulum as used in the static measurement, but it is not fundamentally different in design from the pendulum used in the static measurement.

Since the design differences are too slight to be meaningfully expressed by a different illustration, the same figures are referred to. However, for convenience and performance, each pendulum may be optimized differently. A pendulum optimized for static measurements is constructed so that its center of gravity is low, being approximately 1 to 5 mm below the dimple-flexure contact point, so that the angular difference, θ, is appreciable and easily measurable. A pendulum optimized for dynamic measurements can be of planar structure with a high center of gravity, but preferably no more than 0.5 mm above the dimple-flexure contact point.

Figure 4:
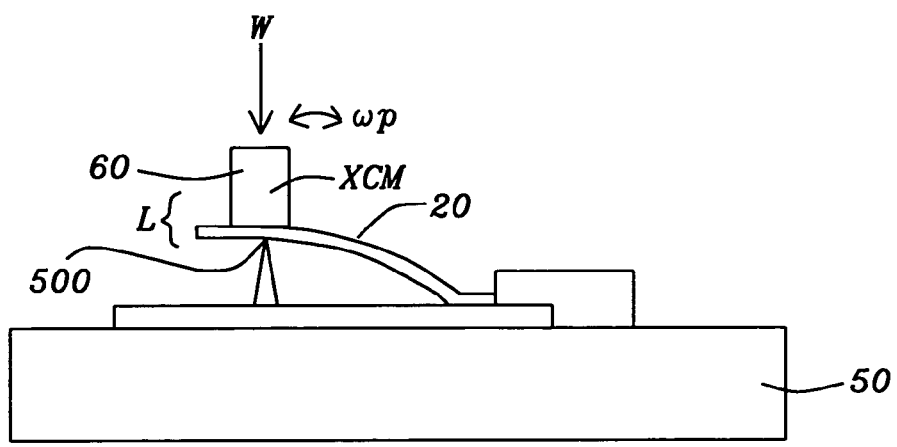
FIG. 4 is a schematic illustration of the pendulum oscillation.

Referring to FIG. 4 for the dynamic measurement, the ABS of the slider (40) has not been tilted through the angle β. The pendulum CM is shown as an X and it is a distance L above the dimple-flexure contact point (500). To measure flexure pitch stiffness, $k_p$, the pendulum (60) is made to vibrate at a natural frequency $\omega_p$ in a pitch direction (as shown) while it remains in contact with the ABS. The displacement of a suitable target on the pendulum (not shown) is monitored continuously by the sensor ((115) in FIG. 2*d*). The natural frequencies of the pendulum oscillations (in either pitch or roll directions or mixed) can be identified from the spectrum produced by the target monitoring, for example, by applying a fast Fourier transform (FFT) to the target displacement (more than adequate signal to noise ratio is obtained). In practice, to obtain pitch stiffness, the pendulum would be excited in the pitch oscillatory mode and monitored at a pitch target alone.

The oscillation can be excited in a variety of ways, a simple disturbance such as a puff of air from a small blower apparatus being perfectly adequate. As in the case of the static equilibrium analysis, the restoration force on the displaced pendulum consists of gravity and flexure reaction (the restoring force due to flexing). The flexure pitch stiffness can be expressed in terms of the angular frequency $\omega_p$ of the flexure in a pitch direction and its moment of inertia, $I_{pivot}$, about the center of dimple contact, when the entire system of pendulum and flexure is in oscillatory motion.

$$k_p = \omega_p^2 I_{pivot} - W(L - r_d), \quad (4)$$

where $r_d$ is the radius of curvature of the dimple contact and W is the weight of the pendulum. By the parallel axis theorem:

$$I_{pivot} = I_{CM} + mL^2 = m(r_g^2 + L^2), \quad (5)$$

where $I_{CM}$ is the moment of inertia of the pendulum about an axis through its center of mass, $r_g$ is the radius of gyration of the pendulum and m is the mass of the oscillating system. On the reasonable assumption that $L << r_g$, then $I_{pivot} \approx I_{CM}$. In a typical pendulum as used in the static portion of this experiment, $r_g = 10$ mm and $L = 1$ mm. For the dynamic measurements, a pendulum with a smaller L is used so the error becomes completely negligible. Finally, this gives:

$$k_p \approx \omega_p^2 I_{CM} - W(L - r_d). \quad (6)$$

If the flexure is eliminated and the pendulum oscillates under the influence of gravity only, its natural frequency is denoted $\omega_0$. Setting $k_p = 0$ in (6), effectively represents the pendulum as oscillating without the reaction of the flexure, gives us the natural frequency of the pendulum:

$$0 \approx \omega_0^2 I_{CM} - W(L - r_d). \quad (7)$$

Subtracting (7) from (6) gives:

$$k_p \approx I_{CM}(\omega_p^2 - \omega_0^2) \quad (8)$$

In (8), the dimple radius of curvature and the pendulum center of gravity do not enter into the calculation. The two values of $\omega_p$ and $\omega_0$ can both be obtained empirically, with coo being measured by placing the pendulum on a bare dimple.

Note that either flexure stiffness, $k_p$ or $k_r$ as it would be measured in the above discussion, excludes the effect of dimple curvature. This treatment is to conform to conventions. In reality, however, the slider air bearing surface (ABS) is affected by the combination of conventional "flexure stiffness" and dimple curvature effect. Thus, for the ABS fly height control, this combination should be used in lieu of the conventional "flexure stiffness." Consequently, the term "$-r_d$" should be omitted in equations (4), (6) and (7) to improve the accuracy of calculations. Furthermore, the contribution of dimple curvature to flexure stiffness, $Wr_d$, can be measured using the novel method described above, by removing the slider and flexure, then placing the pendulum on the bare dimple.

As is understood by a person skilled in the art, the preferred embodiments of the present invention are illustrative of the present invention rather than being limiting of the present invention. Revisions and modifications may be made to methods, processes, materials, structures, and dimensions through which is provided a device for static and dynamic measurements of flexure pitch and roll stiffness under operating conditions and methods for using the device to obtain such measurements, while still providing such a device and its method of use in accord with the present invention as defined by the appended claims.

What is claimed is:

1. A device for statically measuring the pitch or roll stiffness of a flexure mounted slider under prescribed loading conditions, comprising:
   a baseplate having a substantially planar surface, said surface capable of being tilted through a measurable angle, $\alpha$, with the horizontal;
   a dock, having a substantially planar surface mounted on said base plate;
   a lifting mechanism mounted on said base plate, said lifting mechanism being movable in three mutually orthogonal directions relative to the position of said dock;
   a fixture mounted on said lifting mechanism, said fixture being capable of holding and positioning an HGA load beam having a flexure mounted slider affixed thereto, wherein an ABS of said slider is upward facing;
   a movable pendulum, said pendulum having a center of mass and said pendulum including:
      a lower surface denoted a facet, said facet being directly above or directly below said center of mass;
      supporting feet, said supporting feet being capable of movably contacting said substantially planar surfaces of said dock and of thereby maintaining said pendulum in a stable resting position on said dock so that said facet is above said flexure mounted slider and faces said ABS;
      target points at which displacement measurements can be taken;
   and wherein said flexure mounted slider can be positioned horizontally and raised vertically by said lifting mechanism so that said ABS of said slider forcefully contacts said facet and raises said pendulum vertically, whereby said pendulum no longer contacts said dock and whereby said pendulum exerts a load force on said slider.

2. The device of claim 1 further including a displacement sensor, said sensor being capable of measuring displacements of chosen target points on said pendulum.

3. The device of claim 1 wherein said load force corresponds to the conditions of hydrodynamic loading during HDD operating conditions.

4. The device of claim 1 wherein surfaces of the dock whereat said pendulum feet contact said dock are polished to a mirror finish and wherein said pendulum feet include protrusions to prevent stiction with said dock.

5. The device of claim 1 wherein said pendulum center of mass is substantially coincident with a contact region whereat a dimple protruding from said loadbeam contacts an underside of said flexure.

6. The device of claim 5 wherein the center of mass is between 1 mm and 5 mm below said contact region.

7. The device of claim 1 wherein said pendulum is formed of non-ferromagnetic material.

8. The device of claim 2 wherein said displacement sensor is inductively coupled to target regions on said flexure and thereby measures their displacement relative to a given initial position.

9. A device for dynamically measuring the pitch or roll stiffness of a flexure mounted slider under prescribed loading conditions, comprising:
   a baseplate having a substantially planar surface;
   a dock, having a substantially planar surface mounted on said base plate;
   a lifting mechanism mounted on said base plate, said lifting mechanism being movable in three mutually orthogonal directions relative to the position of said dock;
   a fixture mounted on said lifting mechanism, said fixture being capable of holding and positioning an HGA load beam having a flexure mounted slider affixed thereto, wherein an ABS of said slider is upward facing;
   a movable pendulum, said pendulum having a center of mass and said pendulum including:
      a lower surface denoted a facet, said facet being directly above or directly below said center of mass;
      supporting feet, said supporting feet being capable of movably contacting said substantially planar surfaces of said dock and of thereby maintaining said pendulum in a stable resting position on said dock so that said facet is above said flexure mounted slider and faces said ABS;
      target points at which displacement measurements can be taken;
   and wherein said flexure mounted slider can be positioned horizontally and raised vertically by said lifting mechanism so that said ABS of said slider forcefully contacts said facet and raises said pendulum vertically, whereby said pendulum no longer contacts said dock and whereby said pendulum exerts a load force on said slider and whereby said pendulum and said flexure mounted slider can be set into oscillations in a pitch direction, a roll direction or a combination thereof while said load force continues to be exerted.

10. The device of claim 9 further including a displacement sensor, said sensor being capable of measuring displacements of chosen target points on said pendulum.

11. The device of claim 9 wherein the load force corresponds to the conditions of hydrodynamic loading during HDD operating conditions.

12. The device of claim 9 wherein surfaces of the dock whereat said pendulum feet contact said dock are polished to a mirror finish and wherein said pendulum feet include protrusions to prevent stiction with said dock.

13. The device of claim 9 wherein said center of mass is substantially coincident with a contact region whereat a dimple protruding from said loadbeam contacts an underside of said flexure.

14. The device of claim 9 wherein the center of mass is between 1 mm and 5 mm below said contact.

15. The device of claim 9 wherein the center of mass is approximately 0.5 mm above said contact.

16. The device of claim 9 wherein said pendulum is formed of non-ferromagnetic material.

17. The device of claim 10 wherein said displacement sensor is inductively coupled to target regions on said flexure and thereby measures their displacement relative to a given initial position.

18. A static method for measuring flexure pitch or roll stiffness while the flexure has a slider mounted thereon and is under a prescribed load, comprising:

providing an HGA, said HGA including a flexure mounted slider whose stiffness under prescribed load is to be measured, said slider having an ABS and a point on said flexure being contacted by a dimple protruding from said HGA;

affixing said HGA to a measuring device, said device further comprising;

a tiltable baseplate;

a movable lifting mechanism fastened to said baseplate, said HGA being affixed to said lifting mechanism whereby the ABS of said slider is placed in an upward facing position;

a dock, having a substantially planar surface, mounted on said baseplate and surrounding said lifting mechanism;

a movable pendulum, supported by feet, resting on said dock, said pendulum having a downward facing bottom surface, denoted a facet, positioned directly above said ABS and wherein the center of mass of said pendulum is directly below said ABS; then by a series of successive horizontal and vertical movements of the lifting mechanism, forcefully contacting said facet with the ABS of said slider, thereby raising said pendulum until it no longer contacts said dock, thereby loading said flexure; then tilting said baseplate through an angle $\alpha$ with the horizontal, whereby said ABS is displaced through a resulting angle $\beta$; then measuring, using a displacement sensor, angles $\beta$ and $\theta=\alpha-\beta$ and computing a stiffness coefficient therefrom.

19. The method of claim 18 wherein the loading corresponds to the conditions of hydrodynamic loading during HDD operating conditions.

20. The method of claim 18 wherein said center of mass is substantially coincident with a contact region whereat a dimple protruding from said HGA contacts an underside of said flexure.

21. The method of claim 18 wherein the center of mass is between 1 mm and 5 mm below said contact.

22. The method of claim 18 wherein said pendulum is formed of non-ferromagnetic material.

23. The method of claim 18 wherein, subsequent to tilting said baseplate, said slider mounted flexure is placed in a condition of static equilibrium whereby said pitch stiffness coefficient is given by $k_p \approx WL\, \beta/\theta = WL(\alpha/\theta - 1)$.

24. A dynamic method for measuring flexure pitch or roll stiffness while the flexure has a slider mounted thereon and is under a prescribed load, comprising:

providing an HGA, said HGA including a flexure mounted slider whose stiffness under prescribed load is to be measured, said slider having an ABS and a point on said flexure being contacted by a dimple protruding from said HGA;

affixing said HGA to a measuring device, said device further comprising;

a baseplate;

a movable lifting mechanism fastened to said baseplate, said HGA being affixed to said mechanism whereby the ABS of said slider is placed in an upward facing position;

a dock, having a substantially planar surface, mounted on said baseplate and substantially surrounding said lifting mechanism;

a movable pendulum, supported by feet, resting on said dock, said pendulum having a downward facing bottom surface, denoted a facet, positioned directly above said ABS and wherein the center of mass of said pendulum is directly below said ABS; then forcefully contacting said facet with the ABS of said slider, by a series of successive horizontal and vertical movements of said lifting mechanism, thereby raising said pendulum until it no longer contacts said dock, thereby loading said flexure mounted slider; then setting said loaded flexure mounted slider and said pendulum into oscillatory motion in a pitch or roll direction; then measuring a loaded roll or pitch oscillation frequency $\omega_r$ or $\omega_p$ of said motion and calculating a stiffness coefficient $k_r$ or $k_p$ therefrom.

25. The method of claim 24 wherein the pitch stiffness coefficient $k_p$ is obtained from measured unloaded and loaded natural frequencies by satisfying the relationship $k_p \approx I_{CM}(\omega_p^2 - \omega_0^2)$, wherein $I_{CM}$ is the moment of inertial of said pendulum about its center of mass, $\omega_p$ is the measured oscillation frequency in a pitch direction and $\omega_0$ is the oscillation frequency of said pendulum in the absence of a flexure.

* * * * *